United States Patent
Wardlaw et al.

(10) Patent No.: US 6,748,337 B2
(45) Date of Patent: Jun. 8, 2004

(54) METHOD AND APPARATUS FOR PROVIDING QUALITY CONTROL IN AN INSTRUMENT FOR MEDICAL ANALYSIS

(75) Inventors: Stephen C. Wardlaw, Lyme, CT (US); Robert A. Levine, Guilford, CT (US)

(73) Assignee: Wardlaw Partners, LP, Lyme, CT (US)

(*) Notice: Subject to any disclaimer, the term of this patent is extended or adjusted under 35 U.S.C. 154(b) by 98 days.

(21) Appl. No.: 10/021,959

(22) Filed: Dec. 14, 2001

(65) Prior Publication Data

US 2002/0133255 A1 Sep. 19, 2002

Related U.S. Application Data

(60) Provisional application No. 60/275,610, filed on Mar. 14, 2001.

(51) Int. Cl.⁷ .......................... G01N 37/00; G06F 19/00
(52) U.S. Cl. .............................. 702/84; 702/81; 435/6; 25/288
(58) Field of Search ........................ 702/81, 84; 435/6; 250/288

(56) References Cited

U.S. PATENT DOCUMENTS

| | | | |
|---|---|---|---|
| 4,858,154 A | * | 8/1989 | Anderson et al. ............. 702/81 |
| 6,192,320 B1 | * | 2/2001 | Margrey et al. .............. 702/84 |
| 2002/0003210 A1 | * | 1/2002 | Marcus ....................... 250/288 |
| 2003/0064393 A1 | * | 4/2003 | Bass et al. ..................... 435/6 |

OTHER PUBLICATIONS

Information on CLIA Waivers (Clinical Laboratory Improvement Amendments) pp. 1–2.
CLIA Categorization Criteria, pp. 1–2.
CLIA Home Page—Clinical Laboratory Improvement Amendments, pp. 1–2.
Guidance for Clinical Laboratory Improvement Amendments of 1988 (CLIA) Criteria for Waiver; Draft Guidance for Industry and FDA Applications pp. 1–22.

* cited by examiner

Primary Examiner—John Barlow
Assistant Examiner—Aditya Bhat
(74) Attorney, Agent, or Firm—McCormick, Paulding & Huber LLP

(57) ABSTRACT

A method and apparatus for providing quality control in a medical analysis instrument is provided. The method includes the steps of: 1) sending one or more quality control specimens to an operator of the analytical instrument; 2) directly or indirectly communicating control data to the analytical instrument, wherein the control data relates acceptable standards to the analytical instrument; 3) analyzing the quality control specimen using the analytical instrument and thereby creating instrument analysis data; 4) evaluating the instrument analysis data using the control data to determine a functional status of the analytical instrument; 5) providing notice to the operator regarding the functional status of the analytical instrument; and 6) optionally preventing the reporting of patient data from the instrument if the functional status is unacceptable.

9 Claims, 1 Drawing Sheet

METHOD AND APPARATUS FOR PROVIDING QUALITY CONTROL IN AN INSTRUMENT FOR MEDICAL ANALYSIS

This application claims the benefit of U.S. Provisional Patent application serial No. 60/275,610, filed Mar. 14, 2001.

BACKGROUND OF THE INVENTION

1. Technical Field

The present invention relates to instruments for medical analysis in general, and to methods of and apparatus for quality control of medical analysis instruments in particular.

2. Background Invention

Current laboratory practice uses skilled technologists to run quality control specimens in an analytical instrument and compare the results with reference values generally supplied by the manufacturer of the quality control material. It is then left up to the operator's or supervisor's judgement whether or not the instrument is "in control" i.e., whether the instrument is capable of producing correct results with samples from patients. There are many different guidelines published for performing comparisons, but at all times the decision whether or not to release a patient's results is up to the operator or laboratory supervisor. This system functions well when personnel skilled in laboratory sciences are used, but it becomes problematic in situations when the operator is less skilled and may have no direct supervision.

Federal regulatory agencies within the United States (e.g., U.S. Food and Drug Administration) have recently adopted guidelines and standards for laboratory testing to ensure the accuracy, reliability, and timeliness of patient test results. According to those guidelines, certain tests considered to be simple enough so as to be usable by an untrained operator may be subject to reduced regulatory oversight. Tests that fall into this "simple" category are those that either: 1) employ methodologies that are so simple and accurate that there is a negligible chance an untrained operator will get inaccurate results; or 2) have negligible risk of harm should the test be performed incorrectly. Tests having increased complexity or potential risk remain subject to regulatory oversight, and must therefore be performed by a trained professional. The classification of a test as "simple" is based on numerous considerations. For example, if an analytical instrument includes quality control measures that minimize the possibility of erroneous result, tests performed by that instrument are more likely to be subject to less regulatory oversight. Likewise, if an analytical instrument is fully automated and does not require operator technique, tests performed on that instrument are also likely to be subject to less regulatory oversight. It is also important that any such quality control measures be secure and not susceptible to unauthorized operator manipulation or false reporting. Those skilled in the art will recognize the value of enabling more tests to be classified as requiring less regulatory oversight; e.g., the public is likely to have better access to the testing at a lower price.

What is needed, therefore, is a method and/or an apparatus for providing quality control measures for medical analysis instruments that enable an operator, trained or untrained, to perform tests within acceptable guidelines, and a method and/or an apparatus that can make certain tests eligible for less regulatory oversight than was previously required. It is also desirable that any instrument labeled as having "quality control" measures include tamper-proof quality control measures that cannot be easily overridden by an operator.

DISCLOSURE OF THE INVENTION

It is, therefore, an object of the present invention to provide a method and/or an apparatus for providing quality control for medical analysis instruments that enables people, trained or untrained, to perform tests within acceptable guidelines, and a method and/or apparatus that make tests eligible for less regulatory oversight than was previously required.

According to the present invention, a method for providing quality control in a medical analysis instrument is provided. The method includes the steps of: 1) sending one or more quality control specimens to an operator of the analytical instrument; 2) directly or indirectly communicating control data to the analytical instrument, wherein the control data directly or indirectly relates acceptable standards to the analytical instrument; 3) analyzing the quality control specimen using the analytical instrument and thereby creating instrument analysis data; 4) evaluating the instrument analysis data using the control data to determine a functional status of the analytical instrument; 5) providing notice to the operator regarding the functional status of the analytical instrument; and 6) optionally preventing the reporting of patient data from the instrument if the functional status is unacceptable.

The present invention also contemplates a quality control system for analytical instruments that includes: 1) one or more quality control specimens, each having one or more predetermined characteristic values and an identifier that can identify the quality control specimen; 2) an analytical instrument, having an analyzer for analyzing the one or more quality control specimens, and thereby create instrument analysis data that includes one or more sensed characteristic values; 3) means for evaluating the sensed characteristic values of the instrument analysis data using the predetermined characteristic values; and 4) means for notifying an operator regarding the functional status of the analytical instrument.

An advantage of the present method and apparatus is that quality control procedures can be performed on the instrument without the assistance of a laboratory-trained technician. In most instances, the operator need only insert the quality control specimen and the quality control procedures are performed automatically. In other instances, the quality control specimen is provided electronically or automatically and the operator does not have to insert a quality control specimen. As a result, tests performed on the instrument are likely to be eligible for less regulatory oversight.

Another advantage provided by the ability of the present method and apparatus to operate quality control procedures with limited or no operator input is that the instrument is less vulnerable to operator tampering, and requires less operator training and skill for safe operation.

Another advantage of the present method and apparatus is that quality control procedures can be performed often because they require little or no operator input. As a result, the accuracy and reliability of the instrument can be assured often. Verifying the accuracy and reliability of the instrument will enhance the eligibility of the tests performed on the instrument for less regulatory oversight.

Another advantage of the present method and apparatus is that it gives the analytical instrument manufacturer the opportunity to provide a valuable service to its customers, one that can help distinguish it from competitors.

These and other objects, features, and advantages of the present invention will become apparent in light of the detailed description of the present invention.

DETAILED DESCRIPTION OF THE INVENTION

Figure 1:
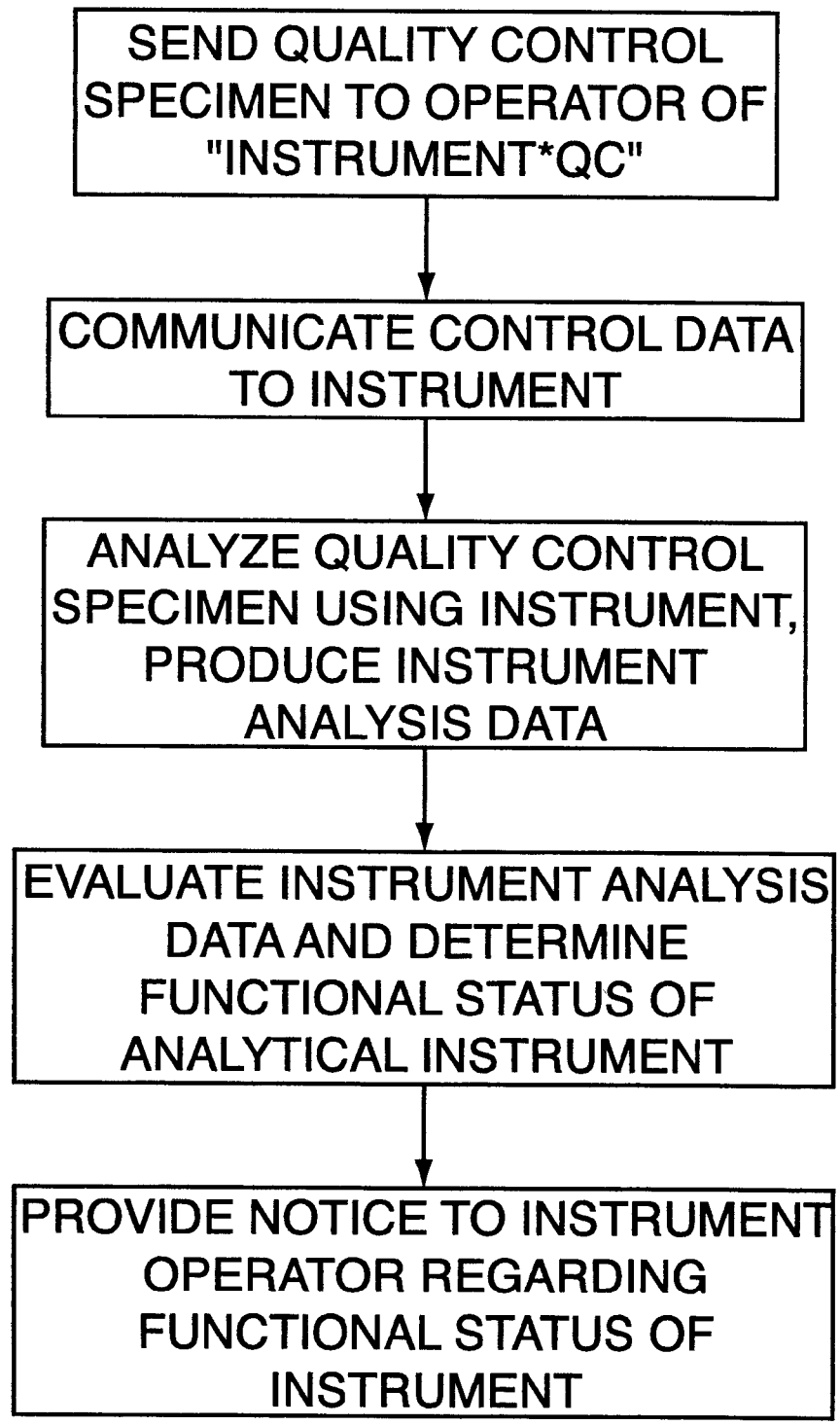
FIG. 1 is a flow chart illustrating the steps of the present method.

Referring to FIG. 1, the present method and apparatus for providing quality control in a medical analysis instrument enables an operator, trained or untrained, to perform a test with an assurance of the quality of the test results. The present method includes the steps of: 1) sending one or more quality control specimens to an operator of the analytical instrument; 2) directly or indirectly communicating control data to the analytical instrument that includes acceptable standards; 3) analyzing the quality control specimen using the analytical instrument and thereby creating instrument analysis data; 4) evaluating the instrument analysis data using the control data to determine a functional status of the analytical instrument; 5) providing notice to the operator regarding the functional status of the analytical instrument; and 6) optionally preventing the reporting of patient data from the instrument if the functional status is unacceptable.

The nature of the one or more quality control specimens sent to the operator will depend on the test at hand and the analytical instrument. The specimen will have characteristics that are the same as, or that simulate, those characteristics within a sample that are sensed by the analytical instrument during the test(s) at hand. For example, if the analytical instrument is designed to test blood samples for certain characteristics, the quality control specimen will likely include a fluid that simulates the blood sample characteristics normally sensed by the analytical instrument. Likewise, if the analytical instrument is designed to test urine samples, the quality control specimen will likely include a fluid that simulates the characteristics of the urine sample normally sensed by the analytical instrument. Quality control specimens can be "sent" to the operator in a variety of ways. For example, quality control specimen slides can be sent periodically (e.g., monthly, quarterly, etc.) by carrier. Alternatively, some applications may permit the use of electronic quality control specimens, in which case the specimen can be transferred electronically. It is also possible that the quality control specimen can be provided with the analytical instrument. If, for example, an analytical instrument is dedicated to a particular test and if the relevant quality control specimen does not have a "shelf life", then a single quality control specimen can be provided by the instrument manufacturer and sent with the analytical instrument.

Control data that directly or indirectly includes acceptable standards is communicated to the analytical instrument. The control data includes predetermined characteristic values pertaining to the quality control specimen. In some instances, a calibrated "master" analytical instrument is used to sense the quality control specimen to create the predetermined characteristic values included in the control data. In other instances, the quality control specimen is manufactured to predetermined specifications, and those specifications provide the characteristic values that are included as control data. Other methods for providing characteristic values within the control data that reflect the characteristic values of the quality control specimen may be used alternatively. The control data can also include elements to inhibit operator tampering; e.g., encrypted code, etc.

The control data can be communicated to the analytical instrument in a variety of ways. Examples of how the control data can be communicated to the analytical instrument include, but are not limited to: 1) preprogramming code into the analytical instrument (e.g., by the instrument manufacturer); 2) providing a machine-readable label (e.g., bar code, magnetic strip, etc.) attached to the quality control specimen; 3) providing a modem or other electrical communications medium that connects the analytical instrument to a remote source of control data; e.g., the manufacturer of the analytical instrument can be a remote source of control data that is accessible via modem; and/or by 4) providing a magnetic or optical storage medium (e.g., a CD, or a floppy disk, etc.) that is sent with the quality control specimen.

The quality control specimen(s) is periodically analyzed by the operator using the analytical instrument to create instrument analysis data. The analysis is performed using the ordinary procedures for the test at hand for the particular analysis instrument. The presence of the quality control specimen is identified to the analytical instrument prior to, or concurrently with, the analysis. Once the quality control specimen is identified, the analytical instrument is preprogrammed to operate in quality control mode, which includes labeling the data created in the analysis of the quality control specimen as instrument analysis data. The identification of the quality control specimen can be accomplished in a variety of different ways; e.g., information within a machine-readable label, operator input, an identifiable predetermined pattern that can be sensed within the quality control specimen, etc.

In the quality control mode, the instrument analysis data is evaluated using the control data to determine the functional status of the analytical instrument. The evaluation can be in the form of a comparison between the characteristic values determined by the analytical instrument sensing the quality control specimen versus the characteristic values provided within control data. If there is a disparity between the two characteristic value sets, then that disparity (i.e., error magnitude) is compared against standards dictating acceptable deviation ranges, error magnitudes, etc. The evaluation can be performed by a routine(s) preprogrammed into the analytical instrument or it can be sent to a remote location (e.g., the instrument manufacturer) and the evaluated there. Regardless of where the evaluation is performed, evaluations in form other than a comparison may be utilized alternatively. It is also preferred that the evaluation be performed in an environment where it cannot be tampered with by an operator (e.g., via preprogrammed routines within the instrument, or via a remotely located instrument, etc.).

The determination of whether the analytical instrument is operating acceptably or unacceptably is premised on the results of the evaluation. For example, if the error magnitude is within acceptable standards, then an "acceptable signal" is produced that indicates the instrument is performing acceptably. The acceptable signal can then be used to trigger a notice to the operator indicating that the instrument is performing acceptably with respect to that particular test. Conversely, if the error magnitude is outside of acceptable standards, then an "unacceptable signal" is produced that indicates the instrument is performing unacceptably. The unacceptable signal can then be used to trigger a notice to the operator indicating that the instrument is performing unacceptably with respect to that particular test.

The notice provided to the operator can assume a variety of forms, and can be tailored to the test at hand. For example, if the risk associated with the test subject matter is great enough, then the notice may include the analytical instrument changing into a partially or completely inoperable mode. In such a mode, the analytical instrument can also be programmed to not release patient test results. The analytical instrument can be programmed to remain inoperable until competent service personnel resolve outstanding performance issues. The notice may also include a signal to the operator that explicitly describes the functional status of the analytical instrument; e.g., via a screen or other visual medium. On the other hand, if the risk associated with the test subject matter is inconsequential (e.g., because the error magnitude is only slightly outside acceptable standards), then the analytical instrument might be left operational, but a warning may be provided indicating service is needed. In some embodiments, the analytical instrument is prompted to take corrective action by preprogrammed or remotely delivered instructions.

A description of an exemplary embodiment of the present method and apparatus is provided below to fully illustrate the capabilities and advantages of the present method and apparatus.

In an exemplary embodiment, a medical analysis instrument that qualifies for lesser regulatory oversight preferably includes a telephone connection for use with an internal dial-up modem. The modem utilizes a "polite" protocol that does not interfere with normal telephone or data use and as such is "invisible" to the operator. A dedicated Internet connection could be used alternatively, but is unnecessary. The analytical instrument preferably has a unique serial number, password, or other identifier that is known to the manufacturer. As a part of the installation of the instrument at the operator's facility, the instrument's identifier is registered with the manufacturer's database. The identifier enables secure communications between the analytical instrument and the database maintained by the manufacturer or other service provider.

At periodic intervals, the manufacturer or its agent ships a quality control specimen to the operator, and the operator in turn processes the quality control specimen through the analytical instrument. The analytical instrument identifies the quality control specimen as such by information provided within a machine-readable label fixed to a container carrying the quality control specimen. For purposes of establishing regulatory compliance, the quality control specimen can be labeled with an origin identifier such as a batch or a lot number. The specifics of identifying the quality control specimens can vary to suit the application at hand. Instrument analysis data is produced when the quality control sample is processed through the instrument. The instrument analysis data is evaluated by comparing it against the control data and the functional status of the analytical instrument is determined. The analytical instrument preferably saves all the data created each time a quality control specimen is run, and that data can be used subsequently to establish regulatory compliance and/or for troubleshooting if necessary. In the present example, the evaluation is performed within the analytical instrument without input from the operator. As a result, the evaluation is performed according to routines preprogrammed into the instrument and is therefore less susceptible to tampering by an operator, or operator error.

To ensure that the instrument remains "in control" (i.e., calibrated, or adjusted to have the proper sensitivity or precision), the present method and apparatus can be set up so that the patients' results will not be shown or printed until the instrument is instructed to by the manufacturer via a modem (i.e., a "release"), or by instructions internal to the instrument (i.e., having a subsequent "correct" control analysis). In addition, if the quality control specimen is not processed within a predetermined period of time following the date it is sent, the analytical instrument can be programmed to prompt the operator by predetermined means or by instructions accessed via modem. If the quality control specimen is not processed by the operator within a predetermined period of time, the analytical instrument can be disabled for patients' samples until a quality control procedure is performed. The timing of quality control specimen receipt and usage windows should be such that the instrument is never unavailable if the operator is reasonably diligent.

The above-described methodology can be performed centrally at a location remote from the medical analysis instrument (e.g., the instrument manufacturer or a service supplier), or in a combination of central and instrument-based decisions. For example, a "release" could be sent to an analytical instrument after the data is analyzed by a central location, or a set of standards could be sent to the instrument from the central location and those standards would then be used to evaluate the instrument analysis data. In such cases, it is the remote electronic input from the centrally located instrument manufacturer that helps to maintain the instrument operating within acceptable limits. The instrument can be located virtually anywhere (e.g., hospitals, laboratories, clinics, doctor offices, etc.) and be kept functionally operating within acceptable standards using the above-described methodology.

The analytical instrument also preferably stores and/or transmits back to the central location any pertinent data collected during daily/startup self-calibration routines performed by the instrument, so that new or incipient problems can be quickly handled. Additionally, operator usage of disposables can be monitored for marketing purposes or for automated reordering of disposables.

In general terms, the present method makes the analytical instrument a "lock box", which only the correct key can unlock the instrument to let the desired data out. The quality control specimen is analyzed using the control data. If the evaluation indicates the analytical instrument is operating within acceptable standards, the instrument is "unlocked".

In addition, the present method and apparatus also contemplates including an indicator with every instrument that qualifies for lesser regulatory oversight. The indicator puts the operator and/or the patient on notice that the instrument qualifies for lesser regulatory oversight because of its desirable quality control or quality assurance procedures that are periodically tested and acted upon. An indicator of this type would provide the operator and patient with a level of confidence that the results produced by the device are accurate and can be relied upon. An example of such an indicator might be a stylized name such as "[instrument]*QC" or "[instrument]*QA" shown on the instrument or its output, where the "[instrument]" portion of the stylized name represents the specific name of the instrument; e.g., Glucometer*QC or Glucometer*QA, etc., and where the "*" is some character, space or icon separating the instrument name from the "QC" or "QA". The public notice function of the indicator would also help operators distinguish between those devices that are periodically tested by regulation, and those that are not.

Although this invention has been shown and described with respect to the detailed embodiments thereof, it will be understood by those skilled in the art that various changes in form and detail thereof may be made without departing from the spirit and scope of the invention.

What is claimed is:

1. A method for providing quality control in an analytical instrument, said method comprising the steps of:
   sending one or more quality control specimens to an operator of the analytical instrument;
   directly or indirectly communicating control data to the analytical instrument, wherein the control data includes characteristic values for the one or more quality control specimens;
   analyzing the quality control specimen using the analytical instrument and thereby creating instrument analysis data;
   evaluating the instrument analysis data using the control data to determine a functional status of the analytical instrument; and
   providing notice to an operator regarding the functional status of the analytical instrument;
   wherein the control data is communicated to the analytical instrument by a machine-readable label attached to the quality control specimen.

2. A method for providing quality control in an analytical instrument, said method comprising the steps of:
   sending one or more quality control specimens to an operator of the analytical instrument;
   directly or indirectly communicating control data to the analytical instrument, wherein the control data includes characteristic values for the one or more quality control specimens;
   analyzing the quality control specimen using the analytical instrument and thereby creating instrument analysis data;
   evaluating the instrument analysis data using the control data to determine a functional status of the analytical instrument; and
   providing notice to an operator regarding the functional status of the analytical instrument;
   wherein the control data is communicated to the analytical instrument by a machine-readable medium supplied with the quality control specimen.

3. A method for providing quality control in an analytical instrument, said method comprising the steps of:
   sending one or more quality control specimens to an operator of the analytical instrument;
   directly or indirectly communicating control data to the analytical instrument, wherein the control data includes characteristic values for the one or more quality control specimens;
   analyzing the quality control specimen using the analytical instrument and thereby creating instrument analysis data;
   evaluating the instrument analysis data using the control data to determine a functional status of the analytical instrument;
   providing notice to an operator regarding the functional status of the analytical instrument; and
   communicating to the analytical instrument that the quality control specimen is for quality control purposes;
   wherein the step of communicating to the analytical instrument that the quality control specimen is for quality control purposes is performed by the analytical instrument reading a machine-readable label.

4. A method for providing quality control in an analytical instrument, said method comprising the steps of:
   sending one or more quality control specimens to a operator of the analytical instrument;
   directly or indirectly communicating control data to the analytical instrument, wherein the control data includes characteristic values for the one or more quality control specimens;
   analyzing the quality control specimen using the analytical instrument and thereby creating instrument analysis data;
   evaluating the instrument analysis data using the control data to determine a functional status of the analytical instrument; and
   providing notice to an operator regarding the functional status of the analytical instrument;
   wherein notice is provided to the operator by preventing the release of a test result until the functional status of the analytical instrument is acceptable.

5. A method for providing quality control in an analytical instrument, said method comprising the steps of:
   sending one or more quality control specimens to an operator of the analytical instrument;
   directly or indirectly communicating control data to the analytical instrument, wherein the control data includes characteristic values for the one or more quality control specimens;
   analyzing the quality control specimen using the analytical instrument and thereby creating instrument analysis data;
   evaluating the instrument analysis data using the control data to determine a functional status of the analytical instrument;
   providing notice to an operator regarding the functional status of the analytical instrument; and
   providing a preprogrammed schedule for quality control procedures to analytical instrument.

6. The method of claim 5, further including the step of providing notice to the operator that a quality control procedure is scheduled.

7. The method of claim 5, further including the step of disabling the analytical instrument if the scheduled quality control procedure is not performed within a predetermined period of time.

8. The method of claim 5, further including the step of automatically providing notice to a service provider that a scheduled quality control procedure has not been performed within a predetermined period of time.

9. A quality control system for analytical instruments, said system comprising:
   one or more quality control specimens, each having one or more predetermined characteristic values and an identifier that can identify the quality control specimen;
   an analytical instrument, having an analyzer for analyzing the one or more quality control specimens, and thereby create instrument analysis data that includes one or more sensed characteristic values;
   means for evaluating the sensed characteristic values of the instrument analysis data using the predetermined characteristic values to determine a functional status of the analytical instrument, wherein the means for evaluating the sensed characteristic values of the instrument analysis data using the predetermined characteristic values does not require input from an operator;
   means for notifying an operator regarding the functional status of the analytical instrument; and
   means for selectively preventing the reporting of test results in the event the functional status of the analytical instrument is determined to be unacceptable.

* * * * *